US010716800B2

(12) United States Patent
Dahan

(10) Patent No.: US 10,716,800 B2
(45) Date of Patent: Jul. 21, 2020

(54) CONJUGATES OF A PHOSPHOLIPID AND A DRUG FOR THE TREATMENT OF INFLAMMATORY BOWEL DISEASE

(71) Applicant: Ben-Gurion University of the Negev Research and Development Authority, Beer-Sheva (IL)

(72) Inventor: Arik Dahan, Modiln (IL)

(73) Assignee: Ben-Gurion University of the Negev Research and Development Authority, Beer-Sheva (IL)

(*) Notice: Subject to any disclaimer, the term of this patent is extended or adjusted under 35 U.S.C. 154(b) by 0 days.

(21) Appl. No.: 15/206,344

(22) Filed: Jul. 11, 2016

(65) Prior Publication Data
US 2016/0317558 A1 Nov. 3, 2016

Related U.S. Application Data

(63) Continuation of application No. 14/536,703, filed on Nov. 10, 2014, now abandoned, which is a continuation of application No. 13/990,457, filed as application No. PCT/IL2011/050037 on Dec. 1, 2011, now abandoned.

(60) Provisional application No. 61/418,892, filed on Dec. 2, 2010.

(51) Int. Cl.
A61K 31/606 (2006.01)
A61K 47/54 (2017.01)
A61K 31/166 (2006.01)
A61K 9/00 (2006.01)

(52) U.S. Cl.
CPC .......... A61K 31/606 (2013.01); A61K 9/0053 (2013.01); A61K 31/166 (2013.01); A61K 47/544 (2017.08)

(58) Field of Classification Search
CPC .. A61K 31/606; A61K 47/544; A61K 9/0053; A61K 31/166
USPC ........................................................ 514/77
See application file for complete search history.

(56) References Cited

U.S. PATENT DOCUMENTS

| 2002/0049183 | A1 | 4/2002 | Yedgar et al. | |
| 2004/0147485 | A1* | 7/2004 | Kozak | C07F 9/10 514/95 |
| 2007/0117779 | A1 | 5/2007 | Yedgar et al. | |
| 2013/0244982 | A1 | 9/2013 | Dahan | |
| 2015/0065462 | A1 | 3/2015 | Dahan | |

FOREIGN PATENT DOCUMENTS

| IL | 142683 | 6/2004 |
| WO | WO 91/16920 | 11/1991 |
| WO | WO 00/031083 | 6/2000 |
| WO | WO 01/19320 | 3/2001 |
| WO | WO 2011/134669 | 11/2011 |
| WO | WO 2012/073245 | 6/2012 |

OTHER PUBLICATIONS

Podolsky et al. Inflammatory Bowel Disease. The New England Journal of Medicine (1991), vol. 325, p. 1008-1016.*
PubChem [online] CID5284373 [Retrieved on Aug. 18, 2017] Retrieved from the internet <url:https://pubchem.ncbi.nlm.nih.gov/compound/cyclosporin_A>.*
Dahan et al. Journal of Controlled Release (2008), vol. 126, pp. 1-9 (Year: 2008).*
Communication Pursuant to Article 94(3) EPC dated Mar. 21, 2016 From the European Patent Office Re. Application No. 11805239.8.
International Preliminary Report on Patentability dated Jun. 13, 2013 From the International Bureau of WIPO Re. Application No. PCT/IL2011/050037.
International Search Report and the Written Opinion dated Mar. 19, 2012 From the International Searching Authority Re. Application No. PCT/IL2011/050037.
Invitation Pursuant to Rule 137(4) EPC dated Apr. 3, 2014 From the European Patent Office Re. Application No. 11805239.8.
Office Action dated Jan. 18, 2016 From the Israel Patent Office Re. Application No. 226670 and Its Translation Into English.
Official Action dated Jul. 8, 2014 From the US Patent and Trademark Office Re. U.S. Appl. No. 13/990,457.
Restriction Official Action dated Feb. 9, 2016 From the US Patent and Trademark Office Re. U.S. Appl. No. 14/536,703.
Restriction Official Action dated Apr. 22, 2014 From the US Patent and Trademark Office Re. U.S. Appl. No. 13/990,457.
Dahan et al. "A Novel Mechanism for Oral Controlled Release of Drugs by Continuous Degradation of a Phospholipid Prodrug Along the Intestine: In-Vivo and In-Vitro Evaluation of an Indomethacin-Lecitin Conjugate", Journal of Controlled Release, 119: 86-93, 2007.
Dahan et al. "Mode of Administration-Dependent Brain Uptake of Indomethacin: Sustained Systemic Input Increases Brain Influx", Drug Metabolism and Disposition, 35(2): 321-324, 2007.
Dahan et al. "Multiple Efflux Pumps Are Involved in the Transepithelial Transport of Colchicine: Combined Effect of P-Glycoprotein and Multidrug Resistance-Associated Protein 2 Leads to Decreased Intestinal Absorption Throughout the Entire Small Intestine", Drug Metabolism and Diposition, 37(10): 2028-2036, 2009.
Dahan et al. "Segmental-Dependent Membrane Permeability Along the Intestine Following Oral Drug Administration: Evaluation of a Triple Single-Pass Intestinal Perfusion (TSPIP) Approach in the Rat", European Journal of Pharmaceutical Sciences, 36: 320-329, 2009.
Dahan et al. "Small Intestinal Efflux Mediated by MRP2 and BCRP Shifts Sulfasalazine Intestinal Permeability From High to Low, Enabling Its Colonic Targeting", American Journal of Physiology, Gastrointestinal and Liver Physiology, 297(2): G371-G377, Aug. 2009.

(Continued)

Primary Examiner — Tina D Matos Negron

(57) ABSTRACT

Conjugates of drugs suitable for use in the treatment of inflammatory bowel disease and phospholipids, and their use in the treatment of inflammatory bowel disease, are disclosed. The disclosed conjugates serve as targeted prodrugs which are suitable for oral administration, and which are capable of releasing the drug selectively at the diseased tissue upon activation by $PLA_2$.

6 Claims, 2 Drawing Sheets

(56) References Cited

OTHER PUBLICATIONS

Dahan et al. "The Oral Absorption of Phospholipid Prodrugs: In Vivo and In Vitro Mechanistic Investigation of Trafficking of A Lecithin-Valproic Acid Conjuugate Following Oral Administration", Journal of Controlled Release, XP022441719, 126(1): 1-9, Nov. 7, 2008. Abstract.

Dvir et al. "DP-155, A Lecithin Derivative of Indomethacin, Is a Novel Nonsteroidal Antiflammatory Drug for Analgesia and Alzheimer's Disease Therapy", CNS Drug Revirews, 13(2): 260-277, 2007.

Frieri et al. "Mucosal 5-Aminosalicyclic Acid Concentration Inversely Correlates With Severity of Colonic Inflammation in Patients With Ulcerative Colitis", Gut, 47: 410-414, 2000.

Haapamaki et al. "Elevated Group II Phospholipase A2 Mass Concentration in Serum and Colonic Mucosa in Crohn's Disease", Clinical Chemistry and Laboratory Medicine, 36(10): 751-755, Oct. 1998.

Haapamaki et al. "Gene Expression of Group II Phospholipase A2 in Intestine in Crohn's Disease", The American Journal of Gastroenterology, 94(3): 713-720, 1999.

Haapamaki et al. "Gene Expression of Group II Phospholipase A2 in Intestine in Ulcerative Colitis", Gut, 40: 95-101, 1997.

Kesisoglou et al. "Novel Drug Delivery Strategies for the Treatment of Inflammatory Bowel Disease", Expert Opinion on Drug Delivery, 2(3): 451-463, May 2005.

Klotz et al. "Topical Delivery of Therapeutic Agents in the Treatment of Inflammatory Bowel Disease", Advanced Drug Delivery Reviews, 57: 267-279, 2005.

Kurz et al. "Drug-Phospholipid Conjugates as Potential Prodrugs: Synthesis, Characterization, and Degradation by Pancreatic Phospholipase A2", Chemistry and Physics of Lipids, 107: 143-157, 2000.

Laye et al. "Phospholipase A2 Expression in Tumours: A Target for Therapeutic Intervention?", Drug Discovery Today, DDT, 8(15): 710-716, Aug. 2003.

Lilja et al. "Phospholipase A2 Gene Expression and Activity in Histologically Normal Ileal Mucosa and in Crohn's Ileitis", Gut, 37: 380-385, 1995.

Minami et al. "Increased Group II Phsopholipase A2 in Colonic Mucosa of Patients With Crohn's Disease and Ulcerative Colitis", Gut, 35: 1593-1598, 1994.

Murakami et al. "Phospholipase A2", Journal of Biochemistry, 131(3): 285-292, 2002.

Peterson et al. "Phospholipase A2 Activating Protein and Idiopathic Inflammatory Bowel Disease", Gut, 39: 698-704, 1996.

\* cited by examiner

CONJUGATES OF A PHOSPHOLIPID AND A DRUG FOR THE TREATMENT OF INFLAMMATORY BOWEL DISEASE

RELATED APPLICATIONS

This application is a continuation of U.S. patent application Ser. No. 14/536,703 filed on Nov. 10, 2014, which is a continuation of U.S. patent application Ser. No. 13/990,457 filed on May 30, 2013, which is a National Phase of PCT Patent Application No. PCT/IL2011/050037 having International filing date of Dec. 1, 2011, which claims the benefit of priority under 35 USC § 119(e) of U.S. Provisional Patent Application No. 61/418,892 filed on Dec. 2, 2010. The contents of the above applications are all incorporated by reference as if fully set forth herein in their entirety.

FIELD AND BACKGROUND OF THE INVENTION

The present invention, in some embodiments thereof, relates to pharmacology and, more particularly, but not exclusively, to a novel methodology for the treatment of inflammatory bowel diseases.

Inflammatory bowel disease, or IBD, is a collective term encompassing related, but distinct, chronic inflammatory disorders of the gastrointestinal tract, such as Crohn's disease, ulcerative colitis (UC), indeterminate colitis, microscopic colitis and collagenous colitis, with Crohn's disease and ulcerative colitis being the most common diseases. Ulcerative colitis is confined to the large intestine (colon) and rectum, and involves only the inner lining of the intestinal wall. Crohn's disease may affect any section of the gastrointestinal tract (e.g., mouth, esophagus, stomach, small intestine, large intestine, rectum and anus) and may involve all layers of the intestinal wall. Both diseases, as well as other IBDs, are characterized by abdominal pain and cramping, diarrhea, rectal and/or intestinal bleeding, weight loss and fever. The symptoms of these diseases are usually progressive, and sufferers typically experience periods of remission followed by severe flare-ups. Less frequent, but also possible, IBD symptoms reflect mucosal inflammation of other sections of the GI tract, such as duodenitis, jejunitis and proctitis.

The goal of IBD therapy is to reduce the extent and symptoms of the inflammation, rather than to actually cure the disease (Kesisoglou and Zimmermann, 2005). Aminosalicylates and corticosteroids are the traditional mainstays of IBD therapy. Immunomodulators (e.g. 6-mercaptopurine, its prodrug azathioprine, tacrolimus), antibiotics, and biological response modulators (infliximab) are also commonly used.

The most commonly used medications to treat IBD are anti-inflammatory drugs such as the salicylates. Preparations of salicylate are effective in treating mild to moderate disease and can also decrease the frequency of disease flares when the medications are taken on a prolonged basis. Examples of salicylates include sulfasalazine, olsalazine, and mesalamine. Particularly, sulfasalazine and related drugs having the bioactive 5-amino-salicylic acid (5-ASA) moiety are widely used to control moderate IBD symptoms and to maintain remission. All of these medications are given orally in high doses for maximal therapeutic benefit. However, treatments with these medications is typically accompanied with adverse side effects such as nausea, dizziness, changes in blood chemistry (including anemia and leukopenia), skin rashes and drug dependence.

Corticosteroids are more potent and faster-acting anti-inflammatory drugs in the treatment of IBD, as compared with salicylates. Prednisone, for example, is a corticosteroid commonly used in the treatment of severe cases of IBD. Nevertheless, potentially serious side effects limit the use of corticosteroids to patients with more severe disease. Side effects of corticosteroids usually occur upon long term use and include thinning of the bone and skin, infections, diabetes, muscle wasting, rounding of faces, psychiatric disturbances, and, on rare occasions, destruction of hip joints.

In cases where IBD patients do not respond to salicylates or corticosteroids, medications that suppress the immune system, namely immunosuppressants, are used. Examples of immunosuppressants include azathioprine and 6-mercaptopurine. However, as immunosuppressants may render the patient immuno-compromised and susceptible to other diseases, the use thereof in the treatment of IBD is not recommended.

IBD presents a challenging target for drug delivery (Klotz and Schwab, 2005). Because the original disease pathogenesis and some of the major pathological manifestations are confined to the GIT tissue, an ideal delivery strategy for IBD should result in an elevated concentration of the therapeutic entity in the diseased intestinal tissue with minimal systemic exposure. For example, studies have shown that for 5-aminosalicylic acid (5-ASA), the therapeutic effect in IBD is directly correlated with the drug concentration in the diseased intestinal mucosa (see, FIG. 1) (Frieri et al., 2000).

Current delivery strategies in the treatment of IBD are based on either a delayed release formulation or a chemical modification of the drug molecule. Delayed release of the drug is typically achieved with polymer coating. For instance, Asacol® is an Edugarit S-coated 5-ASA formulation in which 5-ASA is designed to be released at pH >7, which is found in the ileum and further, Pentasa® is an ethylcellulose-coated 5-ASA formulation in which 5-ASA is continuously release over several hours. The chemical modification approach is focused mainly on increasing first-pass hepatic metabolism and thereby reducing systemic drug levels (e.g., budesonide), or linking the drug (mainly 5-ASA) to a carrier via azo bond to reduce the absorption of the complex in the small intestine and thereby targeting the colon; in the colon, bacterial azo-reductases are able to liberate the free drug from the complex, effectively leading to colonic drug targeting (e.g. sulfasalazine, olsalazine and balsalazide).

All these strategies, however, target a region of the intestine (typically the colon), and not the actual diseased tissue itself. This is disadvantageous with respect to drug therapy and patient care, as it essentially leads to a waste of significant portion of the administered dose, and to increased chances of side effects. Additionally, it excludes the use of these drug products in cases where the inflammation is outside of the particular targeted region, e.g., the small intestine in CD patients.

$PLA_2$ (phospholipases $A_2$) represent a family of enzymes that catalyze the hydrolysis of the sn-2 fatty acyl bond of phospholipids (PL), to liberate a free fatty acid and a lysophospholipid (see, FIG. 2). At least 19 enzymes with $PLA_2$ activity have been identified to date; 10 isozymes are secreted from cells ($sPLA_2$), and the others are cytosolic enzymes ($cPLA_2$), however, by definition, all of them hydrolyze the ester bond at the sn-2 position of PL (Murakami and Kudo, 2002; Touqui and Alaoui-El-Azher, 2001). It has been reported that sPLA$_2$ enzymes do not demonstrate any specific fatty acid selectivity (Kurz and Scriba, 2000; Laye and Gill, 2003).

In the past decade, PLA$_2$ expression in the inflamed tissue of IBD patients, both CD and UC, has been consistently reported to be significantly elevated. In CD, significantly increased gene expression of PLA$_2$ was found in both the small and the large intestinal mucosa with active inflammation (Haapamaki et al., 1999a), as well as significantly higher PLA$_2$ mRNA levels and activity in ileal mucosa from CD patients than from controls (FIG. 3A) (Lilja et al., 1995). In the protein level, the mass concentration of group II PLA$_2$ protein was found to be significantly higher in colonic mucosa of CD patients compared to control (Haapamaki et al., 1998; Minami et al., 1994), and the increased level was correlated with the degree of the inflammatory activity in the intestinal wall (Haapamaki et al., 1998). PLA$_2$ activity in CD patients was measured as well, and was reported to be significantly higher (about 5-folds) than that in control subjects, with an association to the degree of inflammation (see, for example, FIG. 3B) (Minami et al., 1994). The situation was not different in UC; significantly increased gene expression of PLA$_2$ was found in inflamed large intestinal mucosa of UC patients compared to control, with an association between the PLA$_2$ mRNA levels and the degree of inflammation (Haapamaki et al., 1997). The concentration of PLA$_2$ protein in the colonic mucosa of UC patients was found to be significantly higher compared with control (Haapamaki et al., 1999b; Minami et al., 1994), and increased activity in the diseased tissue of UC patient was evident as well (FIG. 3C) (Minami et al., 1994; Peterson et al., 1996). Overall, these data clearly indicate that PLA$_2$ levels are elevated in the diseased IBD tissue, and support the theory that PLA$_2$ is involved in the local and generalized pathological processes of IBD, CD and UC.

The present inventors have previously disclosed an exploitation of the esterase enzyme phospholipase A$_2$ (PLA$_2$) to mechanistically target drug molecules to diseased cells. Thus, the present inventors have designed and investigated a series of conjugates of a phospholipid and the non-steroidal anti-inflammatory drug indomethacin and of a phospholipid and valproic acid, differing in the length of the carbonic linker between the PL and the drug moiety (Dahan et al., 2007; Dahan et al., 2008).

WO 91/16920 discloses lipid derivatives of anti-inflammatory drugs, including aspirin, other salicylates and other non-steroidal anti-inflammatory drugs (NSAIDs), which serve as phospholipid prodrugs that are activated by digestive enzymes such as phospholipase A2 and other phospholipases and lysophospholipases, so as to release the drug and provide a steady level of the drug in the bloodstream while reducing toxicity. According to the teachings of WO 91/16920, the phospholipid prodrugs are useful in treating chronic inflammatory diseases such as rheumatoid arthritis and osteoarthritis.

WO 00/31083 discloses phospholipid derivatives of NSAIDs in which the drug is covalently linked to a phospholipid moiety via a bridging group, and which release the NSAID upon enzymatic cleavage at the diseases site. According to the teachings of WO 00/31083, the bridging group is designed to be sensitive to cleavage by phospholipases such as PLA2 that are specifically elevated at the site of the disease.

Additional background art includes Dahan and Amidon, Am. J. Physiol. Gastrointest. Liver Physiol. 2009; Dahan et al., J. Control. Release, 2007; Dahan et al., J. Control. Release, 2008. Dahan and Hoffman, Drug Metab. Dispos., 2007; Dahan and Hoffman, European Journal of Pharmaceutical Sciences, 2005; Dahan and Hoffman, European Journal of Pharmaceutical Sciences, 2006; Dahan and Hoffman, Pharmaceutical Research., 2006; Dahan et al., Drug Metab. Dispos., 2009; and Dvir et al., CNS Drug Rev. 2007.

SUMMARY OF THE INVENTION

While the prior art teaches phospholipid derivatives of anti-inflammatory drugs which are activated by phospholipases so as to release the drug at the diseased site, the prior art fails to teach phospholipid derivatives that can serve as a targeted drug delivery system in the treatment of inflammatory bowel diseases (IBD).

The prior art further fails to teach a targeted drug delivery system that can deliver an active drug to the small intestine, for the treatment of, for example, Crohn's disease in patients with lesions in the small intestine.

The prior art further fails to teach a targeted drug delivery system for the treatment of IBD, which is suitable to be administered as an oral liquid dosage form.

The commonly used drug products for treating IBDs commonly require high daily doses, at least partially to ineffective targeting to the diseased tissue.

The present inventors have now designed a novel methodology for targeting IBD drugs to diseased tissues. This novel methodology enables the treatment of IBD patients with inflamed tissues at the small intestine, and further enables the treatment of IBD patients while utilizing lower daily doses and optionally liquid oral formulations, thus increasing patient's compliance.

According to an aspect of some embodiments of the present invention there is provided a method of treating an inflammatory bowel disease in a subject in need thereof, the method comprising orally administering to the subject a therapeutically effective amount of a conjugate which comprises a drug useful in the treatment of the inflammatory bowel disease covalently linked to a phospholipid.

According to some embodiments of the invention, the conjugate is formulated as a liquid oral formulation.

According to an aspect of some embodiments of the present invention there is provided a use of a conjugate which comprises a drug useful in the treatment of the inflammatory bowel disease covalently linked to a phospholipid in the manufacture of a medicament for treating the inflammatory bowel disease, the medicament being formulated for oral administration.

According to some embodiments of the invention, the medicament is formulated as a liquid oral formulation.

According to an aspect of some embodiments of the present invention there is provided a conjugate comprising a drug useful in the treatment of the inflammatory bowel disease being covalently linked to a phospholipid, the conjugate being identified for use in the treatment of the inflammatory bowel disease via oral administration of the conjugate.

According to some embodiments of the invention, the conjugate is formulated as a liquid oral formulation.

According to an aspect of some embodiments of the present invention there is provided a pharmaceutical composition comprising, as an active ingredient, a conjugate which comprises a drug useful in the treatment of the inflammatory bowel disease covalently linked to a phospholipid, and a pharmaceutically acceptable carrier, the composition being formulated for oral administration and is being packaged in a packaging material and identified in print, in or on the packaging material, for use in the treatment of the inflammatory bowel disease.

According to some embodiments of the invention, the composition is being formulated as a liquid oral formulation.

According to an aspect of some embodiments of the present invention there is provided an oral liquid dosage form comprising a conjugate which comprises a drug useful in the treatment of the inflammatory bowel disease covalently linked to a phospholipid, and a pharmaceutically acceptable carrier.

According to some embodiments of the invention, the inflammatory bowel disease is selected from the group consisting of Crohn's disease and ulcerative colitis.

According to some embodiments of the invention, the inflammatory bowel disease is manifested in the small intestine.

According to some embodiments of the invention, the drug useful in the treatment of inflammatory bowel disease is selected from the group consisting of a salicylate, a corticosteroid, an immunomodulator, an antibiotic and a biological response modulator.

According to some embodiments of the invention, the drug useful in the treatment of inflammatory bowel disease comprises 5-ASA.

According to some embodiments of the invention, the drug useful in the treatment of inflammatory bowel disease is selected from the group consisting of a drug that comprises 5-ASA, tacrolimus and methotrexate.

According to some embodiments of the invention, the phospholipid is a phosphoglycerol.

According to some embodiments of the invention, the drug is linked to position sn-2 of the phosphoglycerol.

According to some embodiments of the invention, the drug is linked to the phospholipid directly.

According to some embodiments of the invention, the drug is linked to the phospholipid via a bridging unit.

According to some embodiments of the invention, the bridging unit comprises an alkylene being from 1 to 20 carbon atoms in length.

According to some embodiments of the invention, the alkylene is being from 3 to 6 carbon atoms in length.

According to some embodiments of the invention, the conjugate has a general Formula:

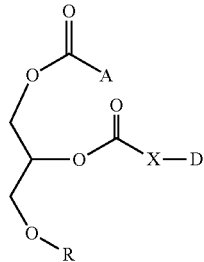

wherein:
A is an alkylene chain being 3-30 carbon atoms in length;
X is the bridging unit or absent;
D is the drug suitable for use in the treatment of the inflammatory bowel disease; and
R is selected from the group consisting of —P(=O)(ORa)(ORb), phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy (propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol, wherein Ra and Rb are each independently selected from the group consisting of hydrogen, alkyl, cycloalkyl and aryl.

According to some embodiments of the invention, the drug comprises 5-ASA.

According to some embodiments of the invention, the drug is selected from the group consisting of a drug that comprises 5-ASA, a mercaptopurine such tacrolimus and methotrexate.

According to some embodiments of the invention, X is an alkylene chain being 3-6 carbon atoms in length.

According to some embodiments of the invention, wherein R is phosphoryl choline.

According to some embodiments of the invention, A is an alkylene chain being 15 or 17 carbon atoms in length.

According to an aspect of some embodiments of the present invention there is provided a process of preparing a conjugate which comprises a phospholipid having attached thereto a drug suitable for the treatment of an inflammatory bowel disease, the process comprising covalently coupling the drug to a lysophospholipid.

According to an aspect of some embodiments of the present invention there is provided a conjugate comprising a phospholipid having attached thereto 5-amino salicylic acid (5-ASA).

According to some embodiments of the invention, the conjugate has a general Formula:

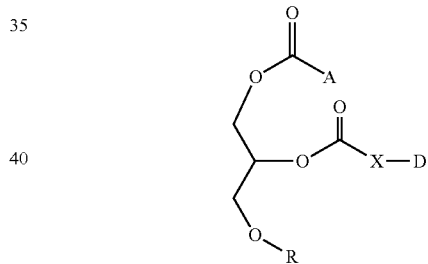

wherein:
A is an alkylene chain being 3-30 carbon atoms in length;
X is a bridging unit or absent;
D is 5-ASA; and
R is selected from the group consisting of —P(=O)(ORa)(ORb), phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy (propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol, wherein Ra and Rb are each independently selected from the group consisting of hydrogen, alkyl, cycloalkyl and aryl.

According to some embodiments of the invention, X is an alkylene chain being 3-6 carbon atoms in length.

According to some embodiments of the invention, R is phosphoryl choline.

According to some embodiments of the invention, A is an alkylene chain being 15 or 17 carbon atoms in length.

According to some embodiments of the invention, there is provided an oral liquid dosage form comprising the PL-5-ASA conjugate as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

In the drawings:

FIG. 1 (Background Art) is graph demonstrating a correlation between IBD mucosal tissue concentrations of 5-ASA and soluble interleukin 2 receptor (sIL-2R) (Frieri et al 2000 Gut);

FIG. 2 (Background Art) illustrates the chemical structure of an exemplary phospholipid (the phosphoglycerol lecithin), with the arrow indicating $PLA_2$ site of action;

Figure 3A:
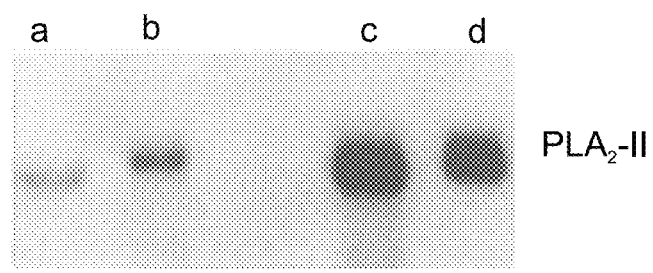
Figure 3B:
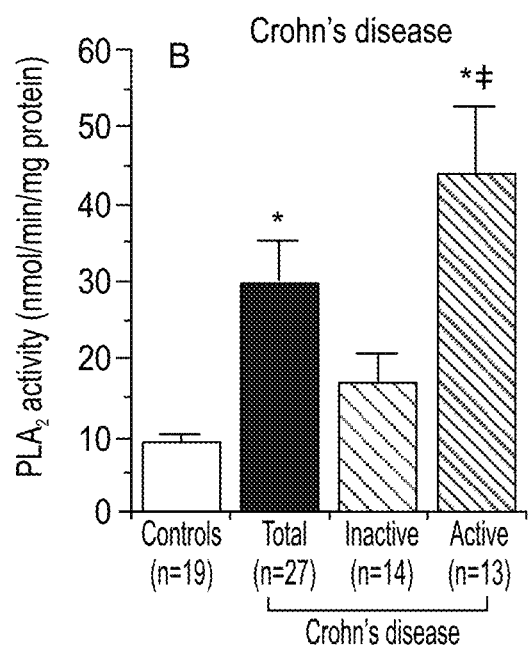
Figure 3C:
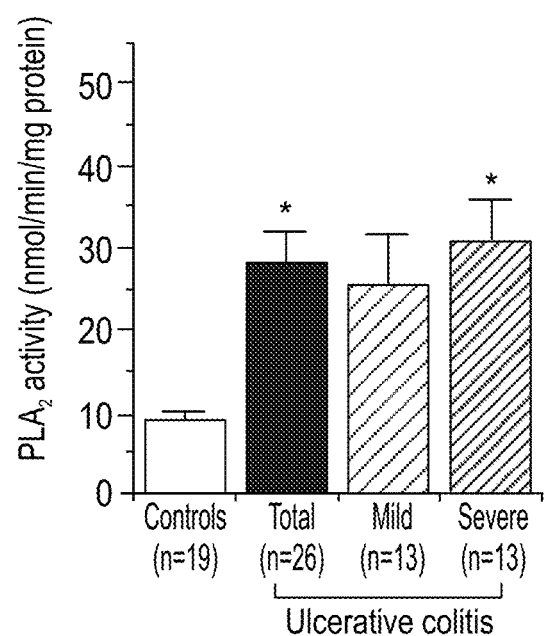

FIG. 3A (Background Art) presents a Northern blot analysis of group II $PLA_2$ mRNA in ileal mucosa from four patients, two controls (a and b) and two CD patients (c and d) (Lilja et al 1995 Gut); and FIGS. 3B and 3C (Background Art) present bar graphs showing $PLA_2$ activity in the colonic mucosa of control and CD patients (FIG. 3B) and UC patient (FIG. 3C) (Minami et al 1994 Gu).

DESCRIPTION OF SPECIFIC EMBODIMENTS OF THE INVENTION

The present invention, in some embodiments thereof, relates to pharmacology and, more particularly, but not exclusively, to a novel methodology for the treatment of inflammatory bowel diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The methodology described herein is aimed at targeting the drug of interest to the diseased tissue per se, in order to improve drug therapy and patient care in IBD, as is detailed hereinbelow.

Based on the findings that $PLA_2$ is overexpressed in the GIT of patients suffering from IBDs, the present inventors have realized that previously described phospholipid derivatives of anti-inflammatory drugs, when administered orally to IBD patients, would release the drug in the GIT, rather than in the blood system. The present inventors have further realized that the overexpression of $PLA_2$ in the GIT of patients suffering from IBDs can be exploited for targeted delivery of anti-inflammatory drugs for treating the IBD.

The present inventors have thus realized that conjugates of a phospholipid and an IBD drug (also referred to herein, interchangeably, as PL-drug conjugates) can be designed and utilized so as to improve therapeutic index and patient care in IBD, based on the following underlying basis.

Since the activation of a PL-drug conjugate as disclosed herein is $PLA_2$-mediated, the increased levels of this enzyme in the diseased tissue leads to increased free drug in the actual diseased tissues, essentially accompanied by decreased drug levels in non-diseased tissues, resulting in extended therapeutic index and improved drug therapy. In fact, it has been realized that the use of conjugates of a phospholipid and an IBD drug provides a "sink effect" since the conjugate acts as a prodrug which is continuously targeted to the diseased tissue and is continuously released in the diseased tissue, as a result of the overexpression of $PLA_2$. Since no accumulation of the prodrug is effected at the diseased tissue, systemic absorption of the drug is reduced, and thus, adverse side effects are reduced. In addition, the amount of free drug at the diseased tissue is increased, and overall, the therapeutic index (efficacy vs. toxicity) is improved.

Notably, the prodrug is targeted to diseased tissues and not to a diseased site, where both diseased and healthy tissues are present, thus avoiding adverse side effects.

It is to be noted that at least some of the currently available IBD drug products are utilized in very high daily oral doses, at least partially due to the poor targeting of the available formulations. Products containing 5-ASA, for example, represent some of the highest oral dose/day medications on the market, with a maximum daily dose of up to 4.8 grams, which sometimes correspond to eight tablets and even more. The targeted delivery of the drug to the inflamed tissue by the disclosed conjugates thus decreases the required dose, leading to improved convenience and better patient compliance.

In addition, unlike the currently available IBD drug products, the conjugates described herein enable specific delivery to diseased tissue throughout the entire gastrointestinal tract (GIT), including the small intestine. It is to be noted that currently available IBD drug products, and 5-ASA products in particular, deliver the drug to the colon, and hence are not effective in treating patients having inflammatory lesions in other tissues, and particularly in small intestine tissues. This is particularly advantageous in the treatment of Crohn's disease patients that have such lesions, and for which current drug therapies are ineffective.

The use of the conjugates described herein further provides for targeted release of the drug without formulation manipulations and hence enables to utilize liquid formulations instead of solid dosage forms (as described hereinabove in the context of formulation manipulations made in order to achieve targeted delivery to certain areas in the GIT). Since the targeting methodology described herein is not formulation-dependent but integral to the PL-drug conjugate molecule, it is possible to formulate it in a liquid oral dosage form without affecting the targeting abilities. This is of great benefit in, for example, pediatric and elderly populations, for whom swallowing of a solid dosage form is impossible/painful. This advantage becomes even more important in light of the large size of most of oral IBD products available on the market.

Finally, the methodology disclosed herein is drug-independent, as it depends on the conjugation to a phospholipid.

Thus, any drug of interest for the treatment of IBD can be utilized and is encompassed by the embodiments of the present invention.

Embodiments of the present invention thus pertain to a novel use of a conjugate of a phospholipid and an IBD drug (PL-drug conjugates), as described herein. While some of the PL-drug conjugates have been previously described in the art, none was described in the context of the methodologies described herein. Embodiments of the present invention also relate to those conjugates of a phospholipid and an IBD drug, which have not been previously described, including, but not limited to, a conjugate of a phospholipid (e.g., a glycerophosphate) and an IBD drug that comprises or consists of 5-ASA, a conjugate of a phospholipid (e.g., a glycerophosphate) and a mercaptopurine such tacrolimus, and a conjugate of a phospholipid (e.g., a glycerophosphate) and methotrexate, each further comprising, optionally, a bridging unit, as described herein.

For any of the aspects of embodiments of the present invention, there are provided conjugates, each comprising a drug useful in the treatment of the inflammatory bowel disease being covalently linked to a phospholipid.

As used herein, the phrase "a drug useful in the treatment of an inflammatory bowel disease", which is also referred to herein interchangeably as "a drug useful in the treatment of an IBD" or as "an IBD drug", or simply as "drug", encompasses any drug that has a therapeutic effect on an inflammatory bowel disease, as the latter is defined herein. This phrase encompasses commercially available drugs, as well as drugs that are under development or that has been suggested as useful in the treatment of an IBD. This phrase further encompasses any pharmaceutically acceptable salt of these drugs, known prodrugs of these drugs, and derivatives of these drugs, and any crystalline form of these drugs (including amorphous form), as these terms are defined herein, all of which are such that exhibit a therapeutic effect on an IBD.

Representative examples of IBD drugs include, but are not limited, salicylates (e.g., aminosalicylates such as drugs comprising 5-amino-salicylic acid (5-ASA), for example, sulfasalazine, olsalazine, and mesalamine); a cortocisteroid (e.g., Prednisone); an immunomodulator (e.g., 6-mercaptopurine, its prodrug azathioprine, tacrolimus); an antibiotic; and a biological response modulator (e.g., infliximab); as well as some anti-cancer agents (e.g., paclitaxel, methotrexate and cyclosporine).

Exemplary drugs include, but are not limited to, 5-ASA, methotrexate, paclitaxel, tacrolimus, colchicine, cyclosporine, Azathioprine, mercaptopurine, Beclomethasone Dipropionate, Infliximab, Traficet-EN, and any other drug for treating an inflammatory bowel disease which is commercially available or is currently under research.

According to some embodiments of the invention, the drug useful in the treatment of inflammatory bowel disease comprises 5-ASA.

By "a drug that comprises 5-ASA" are encompassed 5-ASA itself (e.g., mezalazine) and compounds that are metabolized to release 5-ASA (e.g., sulfasalazine).

Exemplary drugs that comprise 5-ASA include, but are not limited to, mezalazine, sulfasalazine, olsalazine and balsalazide.

Figure 1:
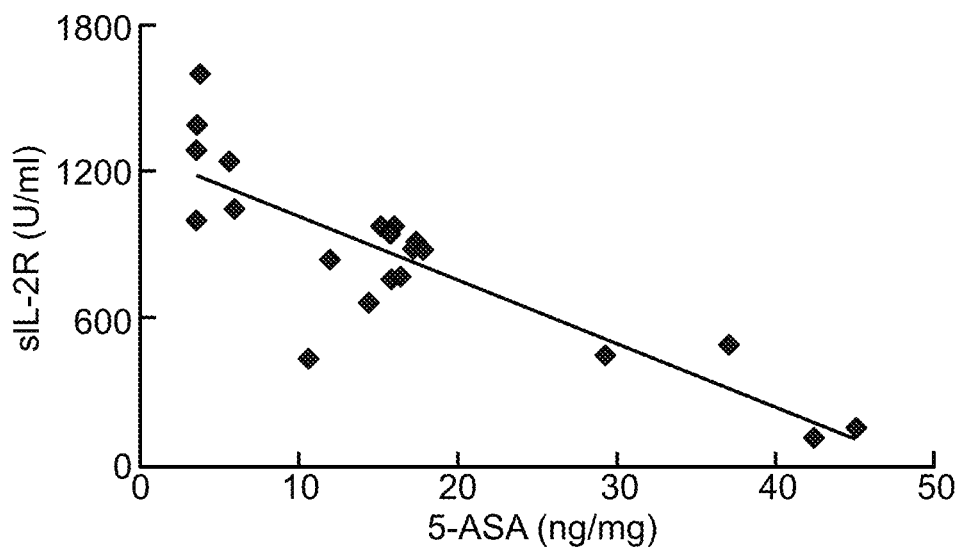
Figure 2:
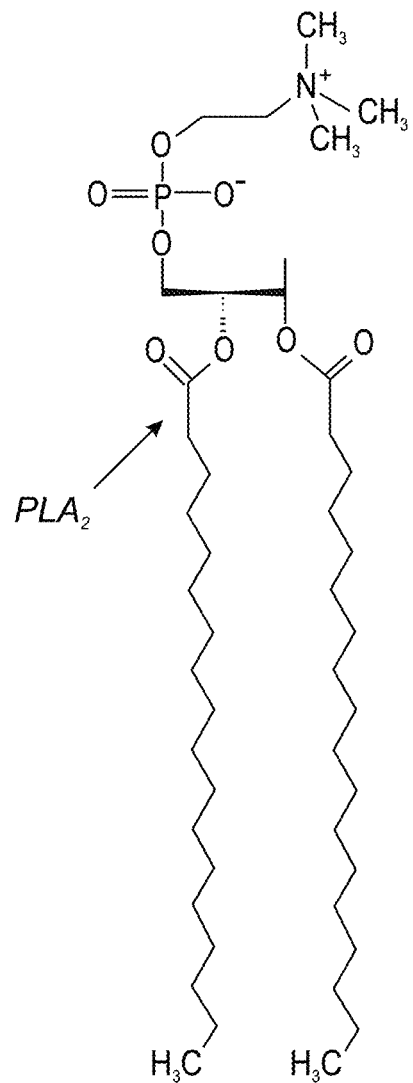

As discussed hereinabove 5-ASA is the mainstay of treatment in IBD. Further, since a correlation has been found between the 5-ASA levels in the inflamed tissue and the therapeutic effect of the drug (see, FIG. 1), an augmented efficacy, as exhibited by the disclosed conjugates, is particularly beneficial.

According to some embodiments of the invention, the drug useful in the treatment of inflammatory bowel disease is methotrextae.

According to some embodiments of the invention, the drug useful in the treatment of inflammatory bowel disease is a mercatopurine such as, for example, tacrolimus.

As used herein, a "phospholipid" describes compounds that comprise a lipid moiety and a phosphate moiety. Commonly available phospholipids are those belonging to the glycerophospholipid class (also known as phosphoglycerols or as diacylglyceride phosphates), including, but not limited to, phosphatidic acid (phosphatidate) (PA), phosphatidylethanolamine (cephalin) (PE), phosphatidylcholine (lecithin) (PC), phosphatidylserine (PS), and phosphoinositides such as, for example, phosphatidylinositol (PI), phosphatidylinositol phosphate (PIP), phosphatidylinositol bisphosphate (PIP2) and phosphatidylinositol triphosphate (PIP3); and those belonging to the phosphosphingolipids class (which are derived from sphongosine), including, but not limited to, ceramide phosphorylcholine (sphingomyelin) (SPH), ceramide phosphorylethanolamine (Cer-PE), and ceramide phosphorylglycerol.

Phosphoglycerols have a glycerolic backbone to which are attached two fatty acyl groups at positions sn-1 and sn-2, and one phosphate moiety at position sn-3.

Phosphosphingolipids have a sphingosine backbone which comprises one unsaturated fatty acyl, and to which are attached one fatty acyl via an amide bond and one phosphate moiety.

According to some embodiments of the invention, the phospholipid is phosphoglycerol.

According to some embodiments of the invention, the drug is linked to position sn-2 of the phosphoglycerol. Such phospholipids are efficient substrates of $PLA_2$.

In some embodiments, the IBD drug is linked to an available phosphglycerol (e.g., lechitin, lysolechitin, phsophinositol, and the like) by replacing the fatty acyl or acyl at position sn-2 of the phosphoglycerol by the drug moiety.

In these embodiments, the phospholipid portion of the conjugate comprises a fatty acyl as present in the phosphoglycerol prior to conjugation, preferably at position sn-1, and a phosphate moiety as present in the phosphglycerol prior to conjugation, at position sn-3.

The term "acyl" as used herein describes a —C(=O)—R moiety, typically derived from the corresponding carboxylate (R'—O—C(=O)—R). The term "fatty acyl" as used herein describes an acyl derived from fatty acid, such that R is a high hydrocarbon chain, typically being at least 2 or at least 3 carbon atoms in length, or from 6 to 30 carbon atoms in length. The hydrocarbon chain can be saturated or unsaturated, the latter can comprise one or more double and/or triple bonds.

In some embodiments, the hydrocarbon chain in a fatty acyl comprises an odd number of carbon atoms, thus being derived from a fatty acid.

Representative examples of fatty acyls are those which comprise a hydrocarbon chain that is derived from palmitic acid, and as such are 15 carbon atoms in length, or from stearic acid, and as such are of 17 carbon atoms in length.

In some embodiments, the drug is linked to the phospholipid via an ester bond.

As used herein, an "ester bond" describes a —O—C(=O)— bond, which is typically formed by reacting a hydroxyl group and a carboxylate or carbonyl group.

In some embodiments, the conjugate comprises a phospholipid that is derived from a glycerophospholipid (a phosphoglycerol), as described herein, in which the IBD drug is attached at position sn-2 of the glycerolic backbone via an ester bond (replacing a fatty acyl of the phosphoglycerol at that position), whereby the other fatty acyl, at position sn-1, and the phosphate moiety at position sn-3 are the same as in the phosphoglycerol.

According to some embodiments of the invention, the IBD drug is linked to the phospholipid directly.

In some embodiments, the IBD drug is linked to the phospholipid directly, via an ester bond, as defined herein. Such conjugates are typically formed by utilizing IBD drugs that have a carboxylate group (e.g., a carboxylic acid group) or by utilizing derivatives of IBD drugs which have been modified to include a carboxylate group or any other reactive group that can form a bond with the hydroxyl group of the phospholipid (see, Example 1 hereinbelow).

According to some embodiments of the invention, the drug is linked to the phospholipid via a bridging unit.

As used herein, a "bridging unit", which is also referred to herein interchangeably as a linking unit, a linking moiety or simply as a linker, is a moiety that is attached to the phospholipid at one end thereof and to the IBD drug at another end thereof, and thus links the IBD drug to the phospholipid.

The bridging unit is typically derived from a suitable precursor, namely, a bifunctional compound that has a first and a second reactive group, as described in detail in Example 1 in the Examples section that follows.

In some embodiments, the bridging unit is desired in cases where the IBD drug utilized does not have a functional group that can form a covalent bond (e.g., an ester bond) with the phospholipid. In these embodiments, the bridging unit can be seen as providing a chemical functionality for attaching the IBD drug to the phospholipid.

In some embodiments, the bridging unit is desired for obviating steric hindrance of the ester bond that is to be subjected to enzymatic hydrolysis (e.g., by $PLA_2$).

Thus, in some embodiments, the desired length of the bridging unit depends, in part, on the size of the linked drug, such that, for example, for bulky drugs, relatively long (e.g. higher than 2 and even higher than 6 carbon atoms) moieties are desired, whereby for relatively small drug molecules, moieties being of 2-6 or from 3-5 carbon atoms in length suffice.

In some embodiments, the bridging unit is 1 carbon atom, 2 carbon atoms, 3 carbon atoms, 4 carbon atoms, 5 carbon atoms, 6 carbon atoms in length, and can be even of 30 carbon atoms or more, in length.

Exemplary bridging units include, but are not limited to, hydrocarbons being from 1 to 30 carbon atoms in length, optionally interrupted by one or more heteroatoms; amino acids; and/or peptides (e.g., short peptides being of 2-10 amino acids).

As used herein, the term "hydrocarbon" encompasses any moiety that comprises carbons and hydrogens covalently linked, in a form of anyone or a combination of alkyl, alkenyl, cycloalkyl, alkynyl and aryl, such that a backbone chain linking the IBD drug to the phospholipid is from 1 to 30 carbon atoms in length, or from 1 to 20, or from 1 to 15, or from 2 to 20, or from 2 to 15, or from 3 to 30, or from 3 to 20, or from 3 to 15, or from 2 to 10, or from 3 to 10, or from 3 to 6, or from 3 to 5, carbon atoms in length.

According to some embodiments of the invention, the bridging unit comprises an alkylene being from 1 to 20 carbon atoms in length, or from 2 to 20 carbon atoms in length, or from 3 to 20 carbon atoms in length, or from 3 to 10 carbon atoms in length, or from 3 to 6, or from 3 to 5 carbon atoms in length.

As used herein, the term "alkylene" describes a hydrocarbon that is comprised of an alkyl chain, which can be represented by $-(CR_cR_d)n-$, wherein Rc and Rd can be the same or different in any unit of the n units in the chain, and each can independently be hydrogen or any of the substituents described herein for an "alkyl".

Alternatively, the bridging unit comprises or is derived from an amino acid or a short peptide (e.g., di- or tri-peptides).

Any of the naturally occurring or non-naturally occurring amino acids, and peptides made therefrom, are contemplated.

In some embodiments, the bridging unit is selected such that upon enzymatic cleavage of the bond connecting it to the phospholipid, the released moiety, which contains the IBD drug, can exert its therapeutic effect.

In some embodiments, the released moiety is the IBD drug having the bridging unit attached thereto (whereby the bridging unit terminates with a functional group generated by the cleavage), and such a moiety is capable of exerting a therapeutic effect comparable to that of the IBD drug per se (namely, the bridging unit does not interfere with the therapeutic activity of the IBD drug).

In some embodiments, the released moiety is the IBD drug having the bridging unit attached thereto (whereby the bridging unit terminates with a functional group generated by the cleavage), and such a moiety is capable of undergoing cleavage under physiological conditions (e.g., a pH-dependent cleavage or an enzymatic cleavage by e.g., esterases, amidases or proteolytic enzymes), so as to release the IBD drug.

In some embodiments, the released moiety is the IBD drug having the bridging unit attached thereto (whereby the bridging unit terminates with a functional group generated by the cleavage), and such a moiety is capable of undergoing self-immolation under physiological conditions as described supra, to thereby release the IBD drug.

In some embodiments, the bridging moiety is selected such that upon release of the IBD drug, by cleavage or self-immolation of the IBD drug having the bridging unit attached thereto (whereby the bridging unit terminates with a functional group generated by the cleavage), a biocompatible moiety is formed (e.g., a metabolite such as, for example, an amino acid or a peptide, urea, and the like).

The PL-drug conjugates described herein can be collectively represented by the following general Formula:

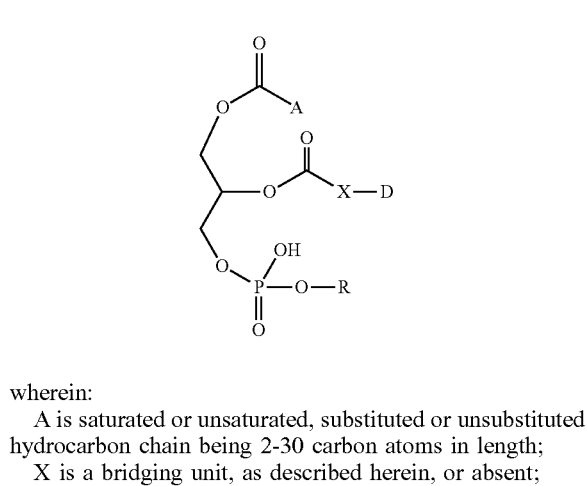

wherein:

A is saturated or unsaturated, substituted or unsubstituted hydrocarbon chain being 2-30 carbon atoms in length;

X is a bridging unit, as described herein, or absent;

D is the drug suitable for use in the treatment of said inflammatory bowel disease (an IBD drug), as described herein; and R is selected from the group consisting of —P(=O)(ORa)(ORb), phosphoryl to choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol, wherein Ra and Rb are each independently selected from the group consisting of hydrogen, alkyl, cycloalkyl and aryl.

In some embodiments, D is a drug that comprises 5-ASA, as defined herein.

In some embodiments, D is a mercaptopurine such as tacrolimus.

In some embodiments, D is methotrexate.

In some embodiments, A is a hydrocarbon chain derived from a fatty acid, as defined herein for a fatty acyl.

In some embodiments, A is a hydrocarbon chain derived from a fatty acid, as defined herein for a fatty acyl, and R is selected from the group consisting of phosphate, phosphoryl choline, phosphoryl serine, phosphoryl enthanolamine, and a phosphoryl inositol.

In some of these embodiments, X can be absent or can be an alkylene of from 3 to 6 carbon atoms.

In some embodiments, A is a hydrocarbon chain derived from a fatty acid, as defined herein for a fatty acyl, R is selected from the group consisting of phosphate, phosphoryl choline, phosphoryl serine, phosphoryl enthanolamine, and a phosphoryl inositol, and D is a drug that comprises 5-ASA, as defined herein.

In some embodiments, A is a hydrocarbon chain derived from a fatty acid, as to defined herein for a fatty acyl, R is selected from the group consisting of phosphate, phosphoryl choline, phosphoryl serine, phosphoryl enthanolamine, and a phosphoryl inositol, and D is a mercaptopurine such as tacrolimus.

In some embodiments, A is a hydrocarbon chain derived from a fatty acid, as defined herein for a fatty acyl, R is selected from the group consisting of phosphate, phosphoryl choline, phosphoryl serine, phosphoryl enthanolamine, and a phosphoryl inositol, and D is methotrexate.

In some of these embodiments, X can be absent or can be an alkylene of from 3 to 6 carbon atoms.

In some embodiments, A is a hydrocarbon chain derived from a fatty acid, as defined herein for a fatty acyl, and D is a drug that comprises 5-ASA, as defined herein.

In some of these embodiments, X can be absent or can be an alkylene of from 3 to 6 carbon atoms.

In some embodiments, A is a hydrocarbon chain derived from a fatty acid, as defined herein for a fatty acyl, and D is a mercaptopurine such as tacrolimus.

In some of these embodiments, X can be absent or can be an alkylene of from 3 to 6 carbon atoms.

In some embodiments, A is a hydrocarbon chain derived from a fatty acid, as defined herein for a fatty acyl, and D is methotrexate.

In some of these embodiments, X can be absent or can be an alkylene of from 3 to 6 carbon atoms.

According to some embodiments, there is provided a conjugate that comprises a drug that comprises 5-ASA as defined herein, being covalently linked to a phospholipid, as defined herein.

In some of these embodiments, the drug is attached to the phospholipid as defined herein, either directly, or via a bridging unit, as defined herein.

According to some embodiments, there is provided a conjugate that comprises any of the IBD drugs as defined herein, being covalently linked to a phospholipid, as defined herein.

In some of these embodiments, the drug is attached to the phospholipid as defined herein, either directly, or via a bridging unit, as defined herein.

In some embodiments, the drug is a mercaptopurine such as tacrolimus.

In some embodiments, the drug is methotrexate.

According to an aspect of some embodiments of the present invention there is provided a process of preparing a conjugate which comprises a phospholipid having attached thereto a drug suitable for the treatment of an inflammatory bowel disease, essentially as described herein. The process is effected by covalently coupling that drug to the phospholipid. In some embodiments, the process is effected by first coupling to the phospholipid a precursor compound for generating the bridging moiety, and then coupling to the obtained phospholipid, having this precursor compound coupled thereto, the IBD drug. Further details regarding the process, according to these embodiments, are described under Example 1 in the Examples section that follows.

In any of the embodiments and aspects of the present invention, the PL-drug conjugate can also be in a form of a pharmaceutically acceptable salt thereof, a hydrate or a solvate thereof, and be in any crystalline form, including an amorphous form.

The term "solvate" refers to a complex of variable stoichiometry (e.g., di-, tri-, tetra-, penta-, hexa-, and so on), which is formed by a solute (the conjugate as described herein) and a solvent, whereby the solvent does not interfere with the biological activity of the solute. Suitable solvents include, for example, ethanol, acetic acid and the like.

The term "hydrate" refers to a solvate, as defined hereinabove, where the solvent is water or an aqueous solution.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a hydroxyl anion (O$^-$) and a cation such as, but not limited to, ammonium, sodium, potassium and the like. Another example, without limitation, of a pharmaceutically acceptable salt would be an ammonium cation and an acid addition salt thereof. Examples of acid addition salts include, but are not limited to, hydrochloric acid addition salt, sulfuric acid addition salt (sulfate salt), acetic acid addition salt, ascorbic acid addition salt, benzenesulfonic acid addition salt, camphorsulfonic acid addition salt, citric acid addition salt, maleic acid addition salt, methanesulfonic acid addition salt, naphthalenesulfonic acid addition salt, oxalic acid addition salt, phosphoric acid addition salt, succinic acid addition salt, sulfuric acid addition salt, tartaric acid addition salt, and toluenesulfonic acid addition salt.

The conjugates described herein can be seen as a prodrug. As used in the art, the term "prodrug" refers to an agent, which is converted into the active compound (the active drug) in vivo. Prodrugs are typically useful for facilitating the administration of the parent drug. In embodiments of the present invention, the conjugate serves as a targeted prodrug, which releases the active drug at a selected tissue (e.g., an inflamed tissue in the GI tract).

As discussed hereinabove, the PL-drug conjugates as described herein can be advantageously utilized in the treatment of an inflammatory bowel disease.

According to an aspect of some embodiments of the present invention there is provided a method of treating an inflammatory bowel disease in a subject in need thereof, the method comprising administering to the subject a therapeutically effective amount of a conjugate which comprises a drug useful in the treatment of the inflammatory bowel disease covalently linked to a phospholipid, as described herein. According to some embodiments of the present invention, administering the described conjugate is effected orally. According to some embodiments of the invention, the conjugate is utilized as a pharmaceutical composition that comprises the conjugate and optionally further comprises a pharmaceutical acceptable carrier, as described herein.

According to an aspect of some embodiments of the present invention there is provided a use of a conjugate which comprises a drug useful in the treatment of the inflammatory bowel disease covalently linked to a phospholipid in the manufacture of a medicament for treating said inflammatory bowel disease. According to some embodiments of the present invention, the medicament is formulated for oral administration. According to some embodiments of the invention, the conjugate is utilized as a pharmaceutical composition that comprises the conjugate and optionally further comprises a pharmaceutical acceptable carrier, as described herein.

According to an aspect of some embodiments of the present invention there is provided a conjugate which comprises a drug useful in the treatment of the inflammatory bowel disease being covalently linked to a phospholipid, and which is identified for use in the treatment of the inflammatory bowel disease. In some embodiments, the conjugate is identified for use via oral administration of the conjugate. According to some embodiments of the invention, the conjugate is utilized as a pharmaceutical composition that comprises the conjugate and optionally further comprises a pharmaceutical acceptable carrier, as described herein.

According to an aspect of some embodiments of the present invention there is provided a pharmaceutical composition comprising, as an active ingredient, a conjugate which comprises a drug useful in the treatment of the inflammatory bowel disease covalently linked to a phospholipid, and a pharmaceutically acceptable carrier. According to some embodiments of the present invention, the composition is formulated for oral administration. According to some embodiments of the present invention, the pharmaceutical composition is packaged in a packaging material and identified in print, in or on said packaging material, for use in the treatment of said inflammatory bowel disease.

As used herein, the phrase "inflammatory bowel disease (IBD)" refers to a disorder or disease characterized by inflammatory activity in the GI tract. Examples of IBDs include, without limitation, Crohn's disease (both distal and proximal), ulcerative colitis, indeterminate colitis, microscopic colitis, collagenous colitis, idiopathic inflammation of the small and/or proximal intestine, irritant bowel syndrome, and IBD-related diarrhea.

In some embodiments, the IBD is manifested in the small intestine. By "manifested in the small intestine" it is meant that at least a portion of the inflamed tissues in the diseased subject are found in the small intestine.

IBDs that can be manifested in the small intestine include, but are not limited to, Crohn's disease and ulcerative colitis.

In some embodiments, the IBD is Crohn's disease. It is to be noted that while IBDs such as, for example, colitis, typically involve inflammation in the large intestine (colon) and/or the ileum, Crohn's disease often involves inflammation in certain regions of the small intestine. Targeting the small intestine is a difficult task to achieve, as described in detail hereinabove and to date, none of the currently available IBD drug therapies can target the small intestine.

In some embodiments, the IBD is associated with overexpression of $PLA_2$ at an inflamed tissue of the GI tract.

In some embodiments, the inflamed tissue is in the small intestine.

It is to be noted that since, in some embodiments, the PL-drug conjugates disclosed herein are designed to release the drug at an inflamed tissue in the GI tract which is associated with overexpression of $PLA_2$, the conjugate of choice can comprise any IBD drug that is suitable for treating the inflammation at this inflamed tissue.

As discussed hereinabove, the conjugates described herein are characterized by an improved therapeutic index, at least compared with the IBD drug when used in a non-conjugated form.

As used herein and known in the art, a "therapeutic index" describes the ratio between the toxic dose of a drug and the therapeutic dose of the drug. This ratio is often defined as $LD_{50}:ED_{50}$. A desirable therapeutically active agent would have an $ED_{50}$ value much higher that the $LD_{50}$ value.

The "sink" effect and other effects exhibited by the disclosed conjugates, as discussed supra provide for an improved efficacy and a reduced toxicity (reduced adverse side effected) of the drug.

In some embodiments, the conjugates described herein are characterized by a therapeutic index that is significantly improved, e.g., improved by at least 10%, or by at least 50%, or even by 100%, as compared to the IBD drug product in which the drug is utilized as a non-conjugated form.

In any of the aspects described herein in the context of treatment of an IBD, the conjugates are utilized in an amount effective to achieve the intended purpose, namely, in a therapeutically effective amount. A therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any of the conjugates as presented herein, the therapeutically effective amount or dose can be estimated initially from activity assays in animals. Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

Dosage amount and interval may be adjusted individually to provide plasma levels of the compounds presented herein which are sufficient to maintain the desired effects, termed the minimal effective concentration (MEC). The MEC will vary for each preparation, but can be estimated from activity data; e.g., the concentration of the conjugates necessary to achieve 50-90% remission of an inflamed tissue. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single or chronic periodic administration, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc.

In some embodiments, the "sink" effect and other effects exhibited by the disclosed conjugates, as discussed supra, enables to use lower daily doses of the conjugate, as compared to a non-conjugated IBD drug product.

In some embodiments, a therapeutically effective amount of the conjugate described herein is lower by at least 10%, at least 20%, at least 30% at least 40% and even by 50%, compared to a corresponding IBD in a non-conjugates form.

A therapeutically effective amount of the conjugate described herein can range from 0.1 to 100 mg/kg body/day, including any value within this range. As noted hereinabove, the conjugates described herein are advantageously utilized as oral formulations.

For oral administration, the conjugate or a pharmaceutical composition or a medicament containing same can be formulated readily by combining the conjugate with pharmaceutically acceptable carriers well known in the art. Such carriers enable the conjugate to be formulated as tablets, pills, dragees, capsules, liquids, gels, syrups, slurries, suspensions, and the like, for oral ingestion by a patient.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

In some embodiments, the conjugate or the composition or medicament containing same are formulated as a liquid formulation for oral administration.

The phrase "liquid formulation for oral administration" is also referred to herein interchangeably as "an oral liquid formulation" or as an "an oral liquid dosage form" and describes a formulation of the conjugate as described herein which is in a liquid form and which can be administered by swallowing the liquid.

By "liquid form" it is meant that a substantial portion of the formulation is liquid. This expression encompasses a solution, in which the conjugate is dissolved or solubilized, a dispersion or suspension of small particles of the conjugate within a liquid solution or an emulsion.

Exemplary liquid dosage forms include solutions, syrups, liquids, slurries, suspensions, emulsions and the like.

In some embodiments, a liquid dosage form comprises an aqueous carrier.

Aqueous carrier for e.g., solutions or, may contain substances, which increase the viscosity of the solution or suspension, such as sodium carboxymethyl cellulose, sorbitol or dextran. Optionally, the suspension may also contain suitable stabilizers or agents, which increase the solubility of the conjugates, to allow for the preparation of highly concentrated solutions.

In some embodiments, a liquid dosage form comprises an oily, lipophilic carrier vehicle.

Exemplary lipophilic solvents or vehicles include fatty oils such as sesame oil, or synthetic fatty acids esters such as ethyl oleate, triglycerides or liposomes.

In some embodiments, a liquid dosage form comprises a flavoring agent.

In some embodiments, a liquid dosage form comprises one or more of a carrier, a co-solvent, a surfactant, a cyclodextrin, and/or a self-emulsifying drug delivery system, including nanosystems.

According to an aspect of some embodiments of the present invention, there is provided an oral liquid dosage form which comprises any of the conjugates described herein.

In some embodiments, there is provided an oral liquid dosage form which comprises a conjugate as described herein, in which the IBD drug comprises 5-ASA, as described herein.

Any of the compositions and formulations described herein may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an IBD, as is detailed hereinabove.

It is expected that during the life of a patent maturing from this application many relevant drugs for treating IBD will be developed and the scope of the term "a drug suitable for use in the treatment of IBD" is intended to include all such new drugs a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. The alkyl group may be unsubstituted or substituted, as long as the substituent does not interfere with the performance and/or intended use of the compound. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be unsubstituted or substituted, as long as the substituent does not interfere with the performance and/or intended use of the compound. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be unsubstituted or substituted, as long as the substituent does not interfere with the performance and/or intended use of the compound. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, indole, indolenine, quinoline, isoquinoline and purine. The heteroaryl group may be unsubstituted or substituted, as long as the substituent does not interfere with the performance and/or intended use of the compound. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be unsubstituted or substituted, as long as the substituent does not interfere with the performance and/or intended use of the compound. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is defined as hereinabove.

A "thiocarbonyl" group refers to a —C(=S)—R' group, where R' is as defined herein.

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An ester bond refers to a —O—C(=O)— bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR"— group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein. A "urea" group refers to an —N(R')—C(=O)—NR"R'" group, where each of R' and R" is as defined herein, and R'" is defined as R' and R" are defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Chemical Syntheses

General Procedure:

The PL-drug conjugates disclosed herein are prepared according to published procedures (see, for example, Dvir et al., 2008 and Kurz and Scriba, 2000).

In an exemplary general procedure, a lysophospholipid, the (IBD) drug of interest and, optionally, a suitable starting material for providing the linker of interest (the bridging moiety), are used as starting materials.

The term "lysophospholipid" as used herein encompasses a derivative of phosphatidic acid in which one of the fatty acid chains has been removed, leaving at the corresponding position a hydroxyl group.

The term "phosphatidic acid", as known in the art, is used to collectively represent fatty acid derivatives of glycerophosphates, which are composed of a glycerol backbone to which 1 mole of phosphoric acid is attached via an ester bond at the terminal 3-hydroxyl group (position sn-3) and 2 moles of fatty acids are attached via an ester bond at the other two hydroxyl groups (at positions sn-1 and sn-2). Conjugation of the fatty acids to the glycerolic backbone results in fatty acyl moieties at positions sn-1 and sn-2.

A "phosphatidic acid" can be represented as follows:

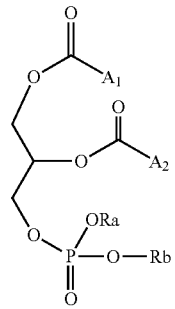

wherein:

A$_1$ and A$_2$ are each independently a saturated or unsaturated hydrocarbon chain being at least 3 carbon atoms in length, as defined herein; and Ra and Rb are each independently hydrogen, alkyl, cycloalkyl, aryl, aminoalkyl, hydroxyalkyl, and the like, or are selected such that the group —P(=O)(ORa)(ORb) represents a phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phosphoglycerol.

Phosphatidic acids that comprise some of the above-indicated phosphoryl groups can be referred to, for example, as phosphatidyl choline, phosphatidyl ethanolamine, phosphatidyl serine, phosphatidyl cardiolipin, phosphatidyl inositol, phosphatidyl ethyl phosphocholine, phosphatidyl methanol, phosphatidyl ethanol, phosphatidyl propanol, phosphatidyl butanol, phosphatidyl ethanolamine-N-lactose, phosphatidyl ethanolamine-N-[methoxy(propylene glycol)], phosphatidyl inositol-4-phosphate, phosphatidyl inositol-4,5-biposphonate, phosphatydil ethanolamine-diethylenetriamine-pentaacetate, and dinitrophenyl-phosphatidyl ethanolamine.

Exemplary lysophospholipids include derivatives of any of the above-described phosphatidic acids, in which the ester bond at position sn-1 or sn-2 has been cleaved into a free fatty acid and a hydroxy group at the respective position of the glycerol backbone.

Lysophospholipids having a hydroxyl group at position sn-1 can be represented by:

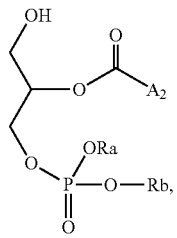

wherein A$_2$, Ra and Rb are as defined herein.

Lysophospholipids having a hydroxyl group at position sn-2 can be represented by:

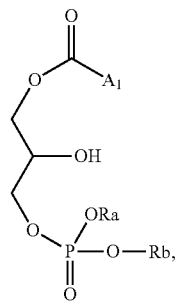

wherein $A_1$, Ra and Rb are as defined herein.

Lysophospholipids having a hydroxyl group at position sn-2, as described herein, are preferred. Such lysophopholipids are also referred to as 1-acyl-2-lyso-phosphoglycerol. An exemplary lysophospholipid is lysolecithin (derived from phosphatidyl choline).

The drug of interest includes any of the drugs suitable for the treatment of an IBD, as described herein, including, for example, 5-ASA, tacrolimus and methotrexate.

The linker of interest can be any of the bridging moieties (or linking moieties) as described herein.

A suitable starting material (precursor) for providing the linker of interest is preferably a bi-functional compound having at one end a first reactive group for forming a bond with the hydroxyl group of the lysophospholipid, and at another end a second reactive group for forming a bond with the drug of interest.

As used herein, the phrase "reactive group", which refers to both the first and the second reactive groups, describes a chemical moiety that is capable of undergoing a chemical reaction that typically leads to a bond formation. The bond, according to some embodiments of the present invention, is preferably a covalent bond. Chemical reactions that lead to a bond formation include, for example, nucleophilic and electrophilic substitutions, nucleophilic and electrophilic addition reactions, cycloaddition reactions, rearrangement reactions and any other known organic reactions that involve a reactive group.

Representative examples of suitable reactive groups according to some embodiments of the present invention include, without limitation, amine, halide, acyl-halide, sulfonate, sulfoxides, hydroxy, alkoxy, aryloxy, thiohydroxy, thioalkoxy, thioaryloxy, cyano, nitro, azo, isocyanate, sulfonamide, carboxylate, thiocarbamate, urea, thiourea, carbamate, amide, guanyl, guanidine and hydrazine, as these terms are defined hereinabove.

In some embodiments, the first and/or second reactive group(s) include, but are not limited to, halide, amine, carboxylate, thiol, alkoxy, aryloxy, thioalkoxy, thioaryloxy, acyl-halide, and anhydride.

In some embodiments, the first reactive group is selected so as to form an ester bond with the hydroxyl group of the lysophospholipid. Such an ester bond is cleavable by $PLA_2$. Suitable first reactive groups therefore include, but are not limited to, carboxylates, acyl halides and anhydrides.

In some embodiments, the second reactive group is selected so as to form a bond with the drug of interest and hence is selected so as to form a bond with a functional group of the drug. In some embodiments, the bond is stable (non-cleavable) under physiological conditions. Exemplary bonds include, without limitation, ester bond, amide bond and thioester bond. Thus, for example, in cases where the drug of interest has a functional group such as amine, thiol or hydroxyl, the second reactive group can be a carboxylate, an anhydride or an acyl halide. In cases where the drug of interest has a functional group such as a carboxylate, the second reactive group can be amine, thiol or hydroxyl. Any "couples" of a second reactive group of the precursor of the bridging moiety and a functional group on the drug of interest, which are compatible one with another by means of forming a bond therebetween, are contemplated.

In an exemplary procedure, where the drug is conjugated directly to the lysophospholipid, the drug of interest preferably comprises a carboxylate (e.g., a carboxylic acid) or, alternatively, is modified so as to comprise a carboxylate. The carboxylate can further be modified to a more reactive group, such as an acyl halide. In some embodiments, prior to being reacted with the lysophospholipid, the carboxylate group on the drug is converted to an acyl chloride or an anhydride, so as to facilitate the reaction. In some embodiments, the reaction is performed in the presence of a coupling agent suitable for esterification (e.g., DCC).

In another exemplary procedure, where the drug is conjugated to the lysophospholipid via a linker, a bifunctional compound selected for providing the linker of interest is reacted with a suitable protecting group, so as to have the second reactive group protected, and the protected compound is reacted with the lysophospholipid. In some embodiment, the protected compound is converted to an anhydride prior to the reaction. Upon the reaction, a protected moiety of the compound is conjugated to the lysophospholipid, and this intermediate is further reacted with the drug by (i) removing to the protecting group, so as to generate the second reactive group; and (ii) reacting with the drug of interest so as to form the desired bond, as described hereinabove.

In any of the above-described general procedures, the chemical structure of obtained product is verified using common analytical procedures (e.g., NMR measurements, such $^1H$, $^{13}C$ and $^{31}P$ NMR spectra, elemental analysis, IR spectroscopy, mass spectrometry and/or UV spectrometry. The purity of the product is determined by high-performance liquid chromatography and/or thin layer chromatography.

If required, purification of the obtained product is performed by common procedures such as, for example, column chromatography, recrystallization, and the like.

Preparation of a Conjugate of 5-ASA and Lysolecithin (Having a 5-Carbon Linker):

A conjugate of 5-ASA and lysolecithin, having the following structure:

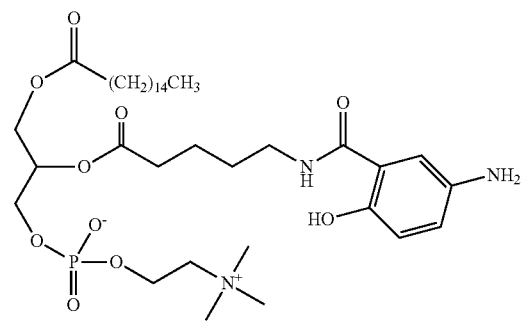

2-(5-(5-amino-2-hydroxybenzamido)pentanoyloxy)-3-(palmitoyloxy)propyl 2-(trimethylammonio)ethyl phosphate
was prepared according to Scheme 1 below.

Preparation of a Series of PL-5-ASA Conjugates:
Following the above-described procedures, a series of conjugates of 5-ASA and various lysophopholipids is prepared. For each lysophopsholipid utilized, the 5-ASA is

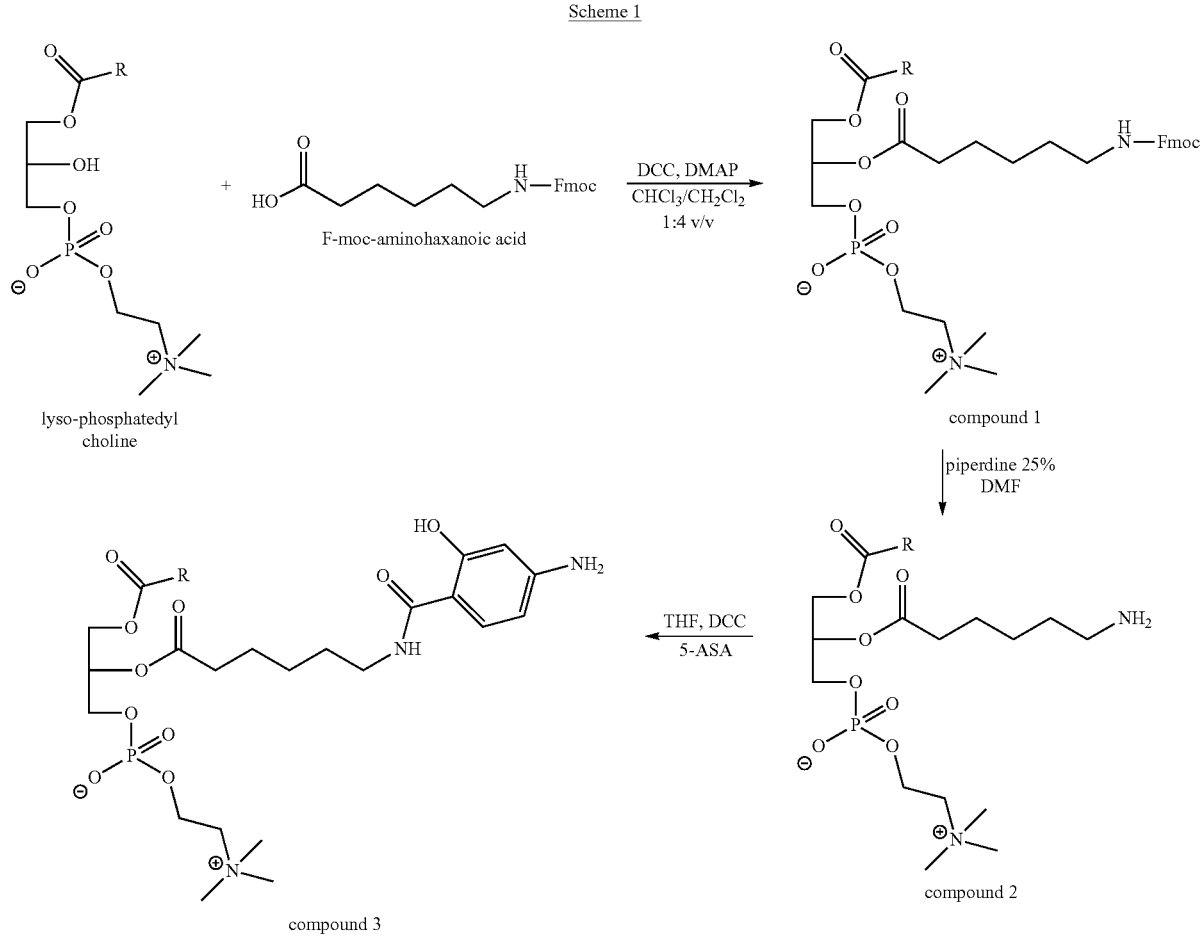

Preparation of Compound 1:
To a solution of Lysophosphatidyl choline (100 mg, 0.2 mmol) and Fmoc-N-aminohexanoic acid (83 mg, 0.24 mmol) in chloroform/dichloromethane 1:4 v/v (5 ml) were added DMAP (5 mg, 0.041 mmol) and DCC (37.08 mg, 0.18 mmol). The mixture was stirred at room temperature for 2 hours. The extract was successively washed with 0.1N HCl, saturated NaHCO$_3$ and water and the solvents were thereafter removed under reduced pressure.

Preparation of Compound 2:
The Fmoc group was removed using 25% piperidine in DMF (6 minutes). Compound 2 was obtained after crystallization with methanol:water (4:1 v/v) and recrystallization with acetone.

Preparation of Compound 3:
Compound 3 was prepared by mixing Compound 2 (200 mg, 1.52 mmol) and 5-ASA (302.59 mg, 1.97 mmol) with DCC (344.98 mg, 1.67 mmol) in THF at 0° C. and stirring the obtained mixture for 1 hour at 0° C., following by stirring at room temperature for 2 hours. The obtained DCU precipitate was removed at the end of the procedure using methanol:water (4:1 v/v).

The product structure is verified as described hereinabove.

attached in the absence of a linker and in presence of various linkers, as described herein.

The disclosed series of PL-5-ASA conjugates is then utilized in various activity studies, for identifying the most potent conjugate for an indicated condition.

Example 2

Degradation by PLA$_2$

PLA$_2$ belongs to a family of enzymes that catalyze the hydrolysis of the sn-2 fatty acyl bond of phospholipids to liberate free fatty acid and lysophospholipid (Kudo and Murakami 2002).

Cleavage of the phospholipid drug conjugates as described herein, in the presence of a PLA$_2$ from is determined as follows:

A mixture of solutions of a phospholipid-drug conjugate (e.g., a PL-5-ASA conjugate as described herein) in ethanol, L-α-phosphatidylcholine and di-o-hexadecyl in Chloroform:MeOH (1:1 v/v), and of phosphatidyl choline (in Chloroform:MeOH 1:1), are evaporated under a stream of nitrogen. Reaction buffer (e.g., containing 300 mM NaCl, 10 mM $CaCl_2$, 25 mM Tris-HCl pH 7.4) is added, and the lipid mixture is sonicated for 10 minutes in a sonication bath, transferred to ice for a few minutes, sonicated for additional 10 minutes, and transferred again to ice.

$PLA_2$ is thereafter added to the tubes, and the obtained solutions are incubated for 1.5 hours at 25° C.

Two types of controls are used: reaction mixture without $PLA_2$; and a reaction mixture that contains $PLA_2$ but do not contain lipids.

Example 3

Intestinal Permeability

The intestinal permeability of the conjugates is assessed to ensure that the intact PL-5-ASA conjugate is not absorbed. The intestinal permeability is evaluated using transepithelial permeability studies across Caco-2 cell monolayers, as previously described [see, for example, Dahan et al., Am. J. Physiol. Gastrointest. Liver Physiol. 2009].

Briefly, $5 \times 10^4$ cells/$cm^2$ are seeded onto collagen-coated membranes (12-well Transwell plate, 0.4-μm pore size, 12-mm diameter, Corning Costar, Cambridge, Mass.) and are allowed to grow for 21 days. Mannitol and Lucifer yellow permeabilities are assayed for each batch of Caco-2 monolayers (n=3), and transepithelial electrical resistance (TEER) measurements are performed on all monolayers (Millicell-ERS epithelial Voltohmmeter, Millipore, Bedford, Mass.). Monolayers with apparent mannitol and Lucifer yellow permeability $<3 \times 10^7$ cm/s and TEER values >300 Qcm2 are used for all studies. On the experiment day, the monolayers are rinsed and incubated for 20 minutes with a blank transport buffer. The transport buffer contains 1 mM $CaCl_2$, 0.5 mM $MgCl_2.6H2O$, 145 mM NaCl, 3 mM KCl, 1 mM $NaH_2PO_4$, 5 mM D-glucose, and 5 mM MES. Similar pH is used in both apical (AP) and basolateral (BL) sides (pH 6.5) to maintain constant degree of ionization in both AP-BL and BL-AP direction experiments and to avoid possible influence of this factor on the permeability across the cells.

Following the 20-minutes incubation, the drug-free transport buffer is removed from the donor side (AP in the AP-BL-direction studies or BL in the BL-AP-direction studies) and replaced by a drug uptake buffer solution (pH 6.5), with or without the tested conjugate. Throughout the experiment, the transport plates are kept in a shaking incubator (50 revolution/minute) at 37° C. Samples are taken from the receiver side at various time points up to 120 minutes (100 μl from BL side or 70 μl from AP side), and similar volumes of blank buffer are added following each sample withdrawal. At the last time point (120 minutes), a sample is taken from the donor side as well to confirm mass balance. Samples are immediately assayed for conjugate content. All Caco-2 monolayers are checked for confluence by measuring the TEER before and after the transport study (TEER values remained steady throughout the experiment).

The intestinal permeability is further evaluated by measuring in-situ intestinal perfusions in a rat model, as previously described [see, for example, Dahan et al., European Journal of Pharmaceutical Sciences. 36:320-329 (2009), which is incorporated by reference as if fully set forth herein.

Briefly, rats are anesthetized with an intra-muscular injection of 1 ml/kg of ketamine-xylazine solution (9%:1%, respectively) and placed on a heated surface maintained at 37° C. (Harvard Apparatus Inc., Holliston, Mass.). The abdomen is opened by amidline incision of 3-4 cm. A proximal jejunal (13.5±1.6 cm average distance of the inlet from the pylorus) or distal ileal segment (14.7±1.8 cm average distance of the inlet from the cecum) of approximately 10 cm is carefully exposed and cannulated on two ends with flexible PVC tubing (2.29 mm i.d., inlet tube 40 cm, outlet tube 20 cm, Fisher Scientific Inc., Pittsburgh, Pa.). Care is taken to avoid disturbance of the circulatory system, and the exposed segment is kept moist with 37° C. normal saline solution. The perfusate is incubated in a 37° C. water bath to maintain temperature, and a perfusion solution containing 10 m MMES buffer, pH 6.5, 135 mM NaCl, 5 mM KCl, and 0.1 mg/ml phenol red with an osmolarity of 290 mosm/l is pumped through the intestinal segment (Watson MarlowPumps 323S, Watson-MarlowBredel Inc., Wilmington, Mass.). The isolated segment is rinsed with blank perfusion buffer, pH 6.5 at a flow rate of 0.5 ml/min in order to clean out any residual debris.

At the start of the study, perfusion solution containing the tested conjugate is perfused through the intestinal segment at a flow rate of 0.2 ml/min. Phenol red is added to the perfusion buffer as a nonabsorbable marker for measuring water flux.

The concentrations of the conjugates used in the perfusion studies are determined by dividing the highest prescribed dose by 250 ml, the standard volume for a glass of water advised to be taken with the dose and hence the accepted minimal gastric volume, in order to represent the maximal drug concentration present in the intestinal segment, and were within their intrinsic solubility reported at pH 6.5 (Avdeef and Berger, 2001; Avdeef et al., 2000). The perfusion buffer is first perfused for 1 hour, in order to assure steady state conditions (as also assessed by the inlet over outlet concentration ratio of phenol red which approaches 1 at steady state). Following reaching to steady state, samples are taken in 10 minutes intervals for 1 hour (10, 20, 30, 40, 50, and 60 min). All samples including perfusion samples at different time points, original drug solution, and inlet solution taken at the exit of the syringe are immediately assayed by HPLC. Following the termination of the experiment, the length of the perfused intestinal segment is accurately measured.

Example 4

In Vivo Studies

PL-5-ASA conjugates which exhibit high activation by $PLA_2$ and low intestinal permeability as an intact conjugate are selected for in vivo studies.

In vivo studies are performed in IBD (UC and CD) models in rats.

Any available IBD rat model can be used. In an exemplary model, mice are lightly anesthetized with halothane, and a 3.5 F catheter is inserted intrarectally 4 cm from the anus. To induce colitis, 100 μL of 3 mg TNBS (Sigma Chemical Co, St. Louis, Mo.) in 50% ethanol (to break the intestinal epithelial barrier) are slowly administered into the lumen via the catheter filled to a 1-mL syringe. Control mice receive 50% ethanol alone (100 μL).

Quantification of $PLA_2$ is performed by Western blotting with a monoclonal antibody against $PLA_2$, as described in, for example, Dahan et al., Drug Metab Dispos., 2009; or otherwise by quantification of PLA2 gene expression, protein content and enzymatic activity, as described, for example, in Haapamaki et al. (1999a), in Lilja et al. (1995)

and/or in Minami et al. (1994), all of which are incorporated by reference as if fully set forth herein.

Pharmacokinetic evaluation of the conjugates activity in the rat model is performed as described, for example, in Dahan and Hoffman 2005, and Dahan and Hoffman 2006, which are incorporated by reference as if fully set forth herein. Pharmacodynamic studies are performed by the SSD rat model for IBD.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Dahan, A., Amidon, G. L., 2009. Small intestinal efflux mediated by MRP2 and BCRP shifts sulfasalazine intestinal permeability from high to low, enabling its colonic targeting. Am. J. Physiol. Gastrointest. Liver Physiol. 297, G371-377.

Dahan, A., Duvdevani, R., Dvir, E., Elmann, A., Hoffman, A., 2007. A novel mechanism for oral controlled release of drugs by continuous degradation of a phospholipid prodrug along the intestine: In-vivo and in-vitro evaluation of an indomethacin-lecithin conjugate. J. Control. Release 119, 86-93.

Dahan, A., Duvdevani, R., Shapiro, I., Elmann, A., Finkelstein, E., Hoffman, A., 2008. The oral absorption of phospholipid prodrugs: In vivo and in vitro mechanistic investigation of trafficking of a lecithin-valproic acid conjugate following oral administration. J. Control. Release 126, 1-9.

Dahan, A., Hoffman, A., 2007. Mode of administration-dependent brain uptake of indomethacin: sustained systemic input increases brain influx. Drug Metab. Dispos. 35, 321-324.

Dahan A. and Hoffman A., 2005. Evaluation of a chylomicron flow blocking approach to investigate the intestinal lymphatic transport of lipophilic drugs. European Journal of Pharmaceutical Sciences. 24:381-388.

Dahan A. and Hoffman A. (2006). Use of a Dynamic in Vitro Lipolysis Model to Rationalize Oral Formulation Development for Poor Water Soluble Drugs: Correlation with in Vivo Data and the Relationship to Intra-Enterocyte Processes in Rats. Pharmaceutical Research. 23:2165-2174.

Dahan, A., Sabit, H., Amidon, G. L, 2009. Multiple efflux pumps are involved in the transepithelial transport of colchicine: Combined effect of P-glycoprotein and MRP2 leads to decreased intestinal absorption throughout the entire small intestine. Drug Metab. Dispos. 37, 2028-2036.

Dvir, E., Elman, A., Simmons, D., Shapiro, I., Duvdevani, R., Dahan, A., Hoffman, A., Friedman, J. E., 2007. DP-155, a lecithin derivative of indomethacin, is a novel nonsteroidal antiinflammatory drug for analgesia and Alzheimer's disease therapy. CNS Drug Rev. 13, 260-277.

Frieri, G., Giacomelli, R., Pimpo, M., Palumbo, G., Passacantando, A., Pantaleoni, G., Caprilli, R., 2000. Mucosal 5-aminosalicylic acid concentration inversely correlates with severity of colonic inflammation in patients with ulcerative colitis. Gut 47, 410-414.

Haapamaki, M. M., Gronroos, J. M., Nurmi, H., Alanen, K., KallaJoki, M., Nevalainen, T J., 1997. Gene expression of group II phospholipase A2 in intestine in ulcerative colitis. Gut 40, 95-101. Haapamaki, M. M., Gronroos, J. M., Nurmi, H., Alanen, K., Nevalainen, T. J., 1999a. Gene expression of group II phospholipase A2 in intestine in Crohn's disease. Am. J. Gastroenterol. 94, 713-720.

Haapamaki, M. M., Gronroos, J. M., Nurmi, H., Irjala, K., Alanen, K., Nevalainen, T. J., 1999b. Phospholipase A2 in serum and colonic mucosa in ulcerative colitis. Scand. J. Clin. Lab Invest. 59, 279-287.

Haapamaki, M. M., Gronroos, J. M., Nurmi, H., Soderlund, K., Peuravuori, H., Alanen, K., Nevalainen, T. J., 1998. Elevated group II phospholipase A2 mass concentration in serum and colonic mucosa in Crohn's disease. Clin. Chem. Lab. Med. 36, 751-755.

Kesisoglou, F., Zimmermann, E., 2005. Novel drug delivery strategies for the treatment of inflammatory bowel disease. Expert Opin. Drug Deliv. 2, 451-463.

Kim, I., Chu, X.-y., Kim, S., Provoda, C. J., Lee, K.-D., Amidon, G. L., 2003. Identification of a human valacyclovirase: Biphenyl hydrolase-like protein as valacyclovir hydrolase. J. Biol. Chem. 278, 25348-25356.

Kim, I., Song, X., Vig, B. S., Mittal, S., Shin, H.-C., Lorenzi, P. J., Amidon, G. L., 2004. A novel nucleoside prodrug-activating enzyme: Substrate specificity of biphenyl hydrolase-like protein. Mol. Pharmaceutics 1, 117-127.

Klotz, U., Schwab, M., 2005. Topical delivery of therapeutic agents in the treatment of inflammatory bowel disease. Adv. Drug Deliv. Rev. 57, 267-279.

Kurz, M., Scriba, G. K. E., 2000. Drug-phospholipid conjugates as potential prodrugs: synthesis, characterization, and degradation by pancreatic phospholipase A2. Chem. Phys. Lipids 107, 143-157.

Lai, L., Xu, Z., Zhou, J., Lee, K.-D., Amidon, G. L, 2008. Molecular basis of prodrug activation by human valacyclovirase, an {alpha}-amino acid ester hydrolase. J. Biol. Chem. 283, 9318-9327.

Laye, J. P., Gill, J. H., 2003. Phospholipase A2 expression in tumours: a target for therapeutic intervention? Drug Discov. Today 8, 710-716.

Lilja, I., Smedh, K., Olaison, G., Sjodahl, R., Tagesson, C., Gustafson-Svard, C., 1995. Phospholipase A2 gene expression and activity in histologically normal ileal mucosa and in Crohn's ileitis. Gut 37, 380-385.

Minami, T., Tojo, H., Shinomura, Y., Matsuzawa, Y., Okamoto, M., 1994. Increased group II phospholipase A2 in colonic mucosa of patients with Crohn's disease and ulcerative colitis. Gut 35, 1593-1598.

Murakami, M., Kudo, I., 2002. Phospholipase A2. J. Biochem. 131, 285-292.

Peterson, J., Dickey, W., Saini, S., Gourley, W., Klimpel, G., Chopra, A., 1996. Phospholipase A2 activating protein and idiopathic inflammatory bowel disease. Gut 39, 698-704.

Touqui, L., Alaoui-El-Azher, M., 2001. Mammalian secreted phospholipases A2 and their pathophysiological significance in inflammatory diseases. Curt. Mol. Med. 1, 739-754.

What is claimed is:

1. A method of treating an inflammatory bowel disease in a subject in need thereof, the method comprising orally administering to the subject a therapeutically effective amount of a conjugate which comprises a drug useful in the treatment of the inflammatory bowel disease covalently linked to a phospholipid, wherein said conjugate has a general Formula:

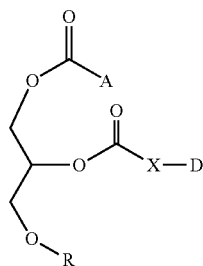

wherein:
A is an alkylene chain being 3-30 carbon atoms in length;
X is a bridging unit;
D is said drug useful in the treatment of said inflammatory bowel disease; and
R is selected from the group consisting of P(=O)(ORa)(ORb), phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol, wherein Ra and Rb are each independently selected from the group consisting of hydrogen, alkyl, cycloalkyl and aryl,
wherein said bridging unit comprises an alkylene of from 8 to 12 carbon atoms in length,
and wherein said drug useful in the treatment of inflammatory bowel disease is cyclosporine.

2. The method of claim 1, wherein the conjugate is administered as a liquid oral formulation.

3. The method of claim 1, wherein R is phosphoryl choline.

4. A method of treating an inflammatory bowel disease in a subject in need thereof, the method comprising orally administering to the subject a therapeutically effective amount of a conjugate which comprises a drug useful in the treatment of the inflammatory bowel disease covalently linked to a phospholipid, wherein said conjugate has a general Formula:

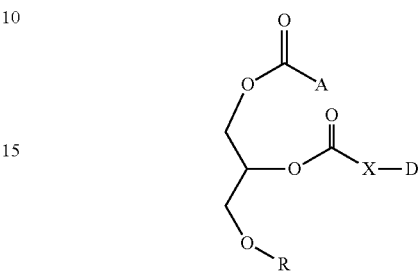

wherein:
A is an alkylene chain being 3-30 carbon atoms in length;
X is a bridging unit;
D is said drug useful in the treatment of said inflammatory bowel disease; and
R is selected from the group consisting of P(=O)(ORa)(ORb), phosphoryl choline, phosphoryl ethanolamine, phosphoryl serine, phosphoryl cardiolipin, phosphoryl inositol, ethylphosphocholine, phosphorylmethanol, phosphorylethanol, phosphorylpropanol, phosphorylbutanol, phosphorylethanolamine-N-lactose, phosphoethanolamine-N-[methoxy(propylene glycol)], phosphoinositol-4-phosphate, phosphoinositol-4,5-biposphonate, pyrophosphate, phosphoethanolamine-diethylenetriamine-pentaacetate, dinitrophenyl-phosphoethanolamine and phsophoglycerol, wherein Ra and Rb are each independently selected from the group consisting of hydrogen, alkyl, cycloalkyl and aryl,
wherein said bridging unit comprises an alkylene of from 8 to 12 carbon atoms in length,
wherein said drug useful in the treatment of inflammatory bowel disease is cyclosporine,
and wherein the conjugate is orally administered as a liquid oral formulation.

5. The method of claim 4, wherein said bridging unit comprises an alkylene of from 10 to 12 carbon atoms in length.

6. The method of claim 4, wherein R is phosphoryl choline.

* * * * *